(12) United States Patent
D'Angelo et al.

(10) Patent No.: US 7,064,133 B2
(45) Date of Patent: Jun. 20, 2006

(54) QUINOLINE DERIVATIVES PROCESS OF SYNTHESIS AND MEDICAMENTS CONTAINING THESE DERIVATIVES

(75) Inventors: Jean D'Angelo, Massy (FR); Christophe Benard, Verriere le Buisson (FR); Michele Danet, Burres sur Yvette (FR); Marc Le Bret, Paris (FR); Jean-Francois Mouscadet, Sceaux (FR); Fatima Zouhiri, Chatenay-Malabry (FR); Marie Bayle, Fontenay aux Roses (FR); Didier Desmaele, Fresnes (FR); Laurence Jeanson, Paris (FR); Herve Leh, Paris (FR); Frederic Subra, Paris (FR)

(73) Assignees: Bioalliance Pharma, Paris (FR); Universite Paris SUD (Paris XI), Orsay (FR); Institut National de la Sante et de la Recherche Medicale (INSERM), Paris (FR); Institut Gustave Roussy, Villejuif (FR); Centre National de la Recherche Scientifique (CNRS)

( * ) Notice: Subject to any disclaimer, the term of this patent is extended or adjusted under 35 U.S.C. 154(b) by 0 days.

(21) Appl. No.: 10/492,088

(22) PCT Filed: Oct. 14, 2002

(86) PCT No.: PCT/FR02/03512

§ 371 (c)(1),
(2), (4) Date: Aug. 18, 2004

(87) PCT Pub. No.: WO03/031413

PCT Pub. Date: Apr. 17, 2003

(65) Prior Publication Data

US 2004/0259911 A1    Dec. 23, 2004

(30) Foreign Application Priority Data

Oct. 12, 2001    (FR) .................................... 0113209

(51) Int. Cl.
*C07D 215/48*    (2006.01)
*A61K 31/47*    (2006.01)

(52) U.S. Cl. ...................... 514/311; 546/169; 514/314

(58) Field of Classification Search ................ 546/169; 514/314, 311
See application file for complete search history.

(56) References Cited

FOREIGN PATENT DOCUMENTS

FR    2 761 687 A    10/1998
WO    WO 98 45269 A    10/1998

OTHER PUBLICATIONS

Zouhiri, F., et al., "Structure-activity relatioships and binding mode of styrylquinolines as Potent inhibitors of HIV-1 Integrase and replication of HIV-1 in Cell Culture", Journal of medicinal Chemistry, American Cehmical Society, Washington, vol. 43, pp. 1533-1540 (2000) XP000926747.

*Primary Examiner*—Zinna Northington Davis
(74) *Attorney, Agent, or Firm*—Foley & Lardner LLP

(57) ABSTRACT

The invention relates to derivatives corresponding to formula I:

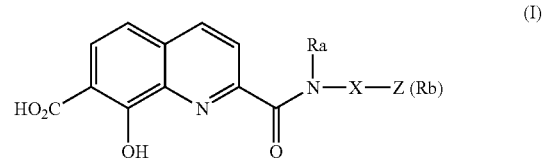

Figure 1A:
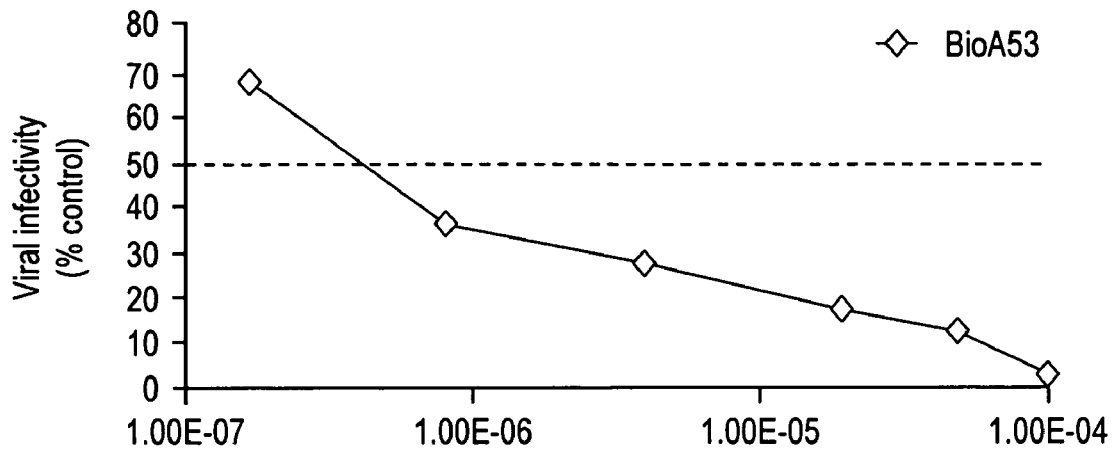

in which
X is an alkyl-$(CH_2)_n$— chain with n=0, 1 or 2, or O or N,
Z is an aromatic which may contain heteroatoms chosen from O, N or S, as substitutions for the carbon atoms constituting said aromatic ring, this ring being substituted or otherwise with Rb,
Rb represents 1 to 3 substituents chosen from —OH, —OR, —COOH, —COOR, —COH, —COR, —NH$_2$, —NH(R), —NH(R,R'), —SH, —SR and CN,
Ra is H or —$(CH_2)_{n'}$—Y, with n'=0, 1, 2 or 3 and Y and —CH$_3$, —COOH, —COOR, —CN, —OH, —OR, SR, or an aryl group optionally substituted with Rb,
R and R' represent a linear or branched alkyl chain of 1 to 4 C, and their pharmaceutically acceptable salts. Application as active ingredient of medicaments inhibiting retrovirus integrases.

12 Claims, 2 Drawing Sheets

QUINOLINE DERIVATIVES PROCESS OF SYNTHESIS AND MEDICAMENTS CONTAINING THESE DERIVATIVES

The subject of the invention is quinoline derivatives possessing in particular retrovirus integrase inhibiting properties. It also relates to a method for synthesizing these derivatives and to the medicaments containing them in their active ingredient.

In application WO 98/45269 in the name of CNRS, quinoline derivatives are described which possess HIV-1 integrase inhibiting properties. On pursuing their work on this type of compound, it has now appeared, unexpectedly, that by producing quinoline derivatives containing both a group identified as being a pharmacophore, at the 7- and 8-positions of the quinoline, and an amide, or an amide derivative, spacer arm between the quinoline and a substituent group of the quinoline ring, it is possible to obtain a novel family which is highly inhibitory of retroviral integrases.

The aim of the invention is therefore to provide novel quinoline derivatives endowed in particular with antiretrovirus integrase properties.

It also relates to a method for synthesizing these derivatives.

According to yet another aspect, the invention also relates to pharmaceutical compositions containing these derivatives.

The quinoline derivatives according to the invention are characterized in that they correspond to formula I

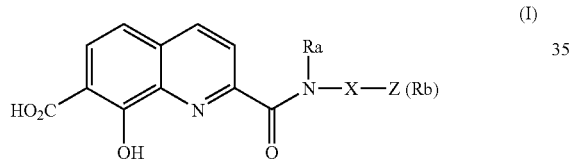

in which
X represents an alkyl-$(CH_2)_n$— chain in which n is equal to 0, 1 or 2, 0, or N,
Z represents an aromatic ring which may contain heteroatoms chosen from O, N or S, as substitutions for the carbon atoms constituting said aromatic ring, it being possible or otherwise for this ring to be substituted with Rb,
Rb represents 1 to 3 identical or different substituents chosen from the groups —OH, —OR, —COOH, —COOR, —COH, —COR, —NH$_2$, —NH(R), —NH(R,R'), —SH and —SR and CN,
Ra represents a hydrogen atom or a group —(CH$_2$)$_{n'}$—Y, for which n' is equal to 0, 1, 2 or 3 and Y represents —CH$_3$, —COOH, —COOR, —CN, —OH, —OR, SR, or an aryl group optionally substituted with Rb,
R and R', which are identical or different, represent a linear or branched alkyl chain of 1 to 4 carbon atoms, and
their pharmaceutically acceptable salts.

Preferred derivatives are 7-carboxy-8-hydroxyquinolines, and their pharmaceutically acceptable salts, chosen from 2-(3,4-dihydroxybenzylcarbamoyl)-8-hydroxyquinoline-7-carboxylic acid, 2-(2,4-dihydroxybenzylcarbamoyl)-8-hydroxyquinoline-7-carboxylic acid and their sodium salts.

The invention also relates to a method for synthesizing the derivatives defined above.

This method is characterized in that it comprises the reaction of a succinimidyl quinolinecarboxylate of formula II

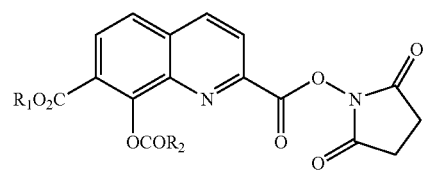

in which $R_1$ and $R_2$, which are identical or different, represent alkyl radicals of 1 to 4C, with an amine of formula III

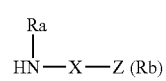

where appropriate in the form of a salt, followed by saponification and where appropriate acidification.

In one embodiment of the invention, to prepare derivatives of formula IA with an amide spacer arm,

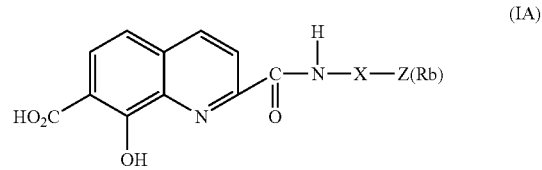

in which Rb and Z are as defined above, and X represents a group —(CH$_2$)$_n$— as defined above, a succinimidyl quinolinecarboxylate of formula II is reacted with an amine salt of the following formula IV:

in which Z and Rb are as defined above, X=(CH$_2$)$_n$ as defined above, and A$^-$ is an anion of an organic salt, or a halide.

The fusion of the succinimidyl quinolinecarboxylate of formula II with the amine salt is carried out in pyridine at room temperature. On carrying out the procedure at about 20° C., the reaction time is of the order of 10 to 15 h.

The amine salt is in particular a para-toluenesulfonate.

The amide Ia is then obtained by saponification, followed by acidification. The saponification is carried out, for example, with a 3N sodium hydroxide solution. This reaction may be performed in methanol at room temperature for about 2 to 4 h, in particular 2 h. For the acidification, dilute sulfuric acid is used in particular.

In another embodiment of the invention, to prepare derivatives of formula IB with a substituted amide spacer arm,

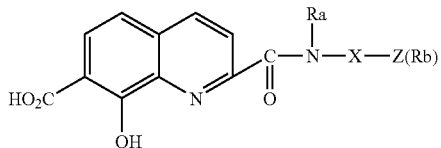

(IB)

in which Rb and Z are as defined above, and X represents a group —(CH$_2$)$_n$— as defined above, the succinimidyl quinolinecarboxylate derivative of formula II is reacted with an amine of the following formula V or its organic salt:

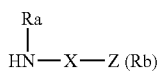

(V)

This reaction is then followed by saponification.

In another embodiment of the invention, to prepare derivatives of formula IC with a hydrazide spacer arm,

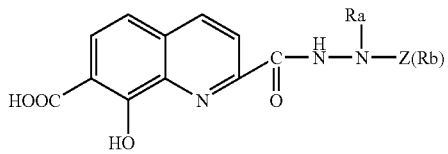

(IC)

in which the different substituents are as defined above, the succinimidyl quinolinecarboxylate of formula II is reacted with the hydrazine of the following formula VI:

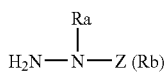

(VI)

In yet another embodiment of the invention, to prepare derivatives of formula ID with an alkoxyamide spacer arm,

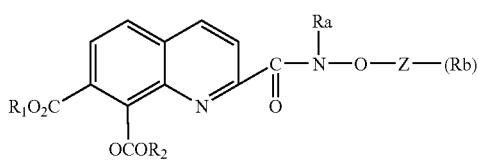

(ID)

in which the different substituents are as defined above, the succinimidyl quinolinecarboxylate of formula II is reacted with the hydroxylamine of the following formula VII:

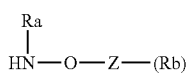

(VII)

Advantageously, the protected derivatives of the succinimidyl quinolinecarboxylate of formula II are obtained from the 8-hydroxy-7-quinaldinecarboxylic acid of formula VIII:

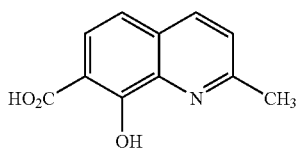

(VIII)

The protection of the —COOH and —OH groups is carried out with the aid of derivatives capable of introducing protecting groups which are specific in relation to the relevant functional groups and which can then be selectively cleaved without adversely affecting the remainder of the molecule.

For example, the —COOH group is first of all esterified, followed by the —OH group.

Satisfactory results were thus obtained by subjecting the hydroxy acid of formula VIII to the action of an aliphatic alcohol, such as methanol or butanol, in the presence of polyphosphoric acid, and then to that of an acyl halide, in particular an acyl chloride, such as pivaloyl chloride, in the presence of pyridine.

The first esterification reaction is carried out at a temperature of the order of 100° C., for about 50 to 80 h, in particular for about 70 h.

The treatment of the ester obtained with an acyl halide is carried out at room temperature in the presence of pyridine, for about 30 min to 2 h, and in particular for 1 h.

The diester derivative obtained is then oxidized in two stages. During the first stage, the —CH$_3$ group in C-2 of quinoline is oxidized to a —COH group, by treating with an agent for oxidizing the —CH$_3$ group, such as selenium oxide. The procedure is advantageously carried out at the reflux temperature of a solvent such as dioxane for about 10 to 15 h, in particular 12 h, so as to obtain the corresponding aldehyde. During a second stage, this aldehyde is then oxidized to an acid. Appropriate oxidizing agents comprise sodium chlorite. By carrying out the procedure in a water/organic solvent (such as t-butanol) mixture, in the presence of sodium dihydrogen phosphate and 2-methyl-2-butene, the corresponding acid is obtained with a satisfactory yield.

To prepare the succinimidyl quinolinecarboxylate of formula II, the —COOH group is activated with the aid of N-hydroxysuccinimide. The fusion of the acid with N-hydroxysuccinimide is advantageously carried out in the presence of dicyclohexylcarbodiimide. By carrying out the procedure at room temperature, of the order of 20° C., the reaction lasts for about 10 to 15 h, in particular 12 h.

The intermediate compounds of formula II are novel compounds and as such also fall within the scope of the invention.

The study of the properties of the derivatives of the invention has made it possible to demonstrate their antiviral activity directed against retroviral integrases, in general, animal and human retroviral integrases, and in particular of HIV-1, HIV-2, SIV, RSV. The efficacy of these derivatives is observed at submicromolar concentrations. IC 50 values not exceeding 1 µM, advantageously 0.5 µM and even 0.1 µM are thus obtained.

These derivatives have furthermore the advantage of great safety and a satisfactory bioavailability of the active drug.

These properties are therefore exploited in accordance with the invention by using these derivatives as active ingredients of medicaments.

The invention therefore relates to pharmaceutical compositions, characterized in that they comprise an effective quantity of at least one derivative as defined above, in combination with pharmaceutically acceptable vehicles.

These compositions are advantageously used in combination with other anti-HIV medicaments, in particular medicaments endowed with an inhibitory effect toward reverse transcriptase and/or protease.

The dosages and the modes of administration will be adjusted according to the mono- or polytherapy treatment used.

The invention also relates to the use of the derivatives defined above as biological reagents which can be used in particular for studies of mechanisms relating to viral infection.

Figure 1B:
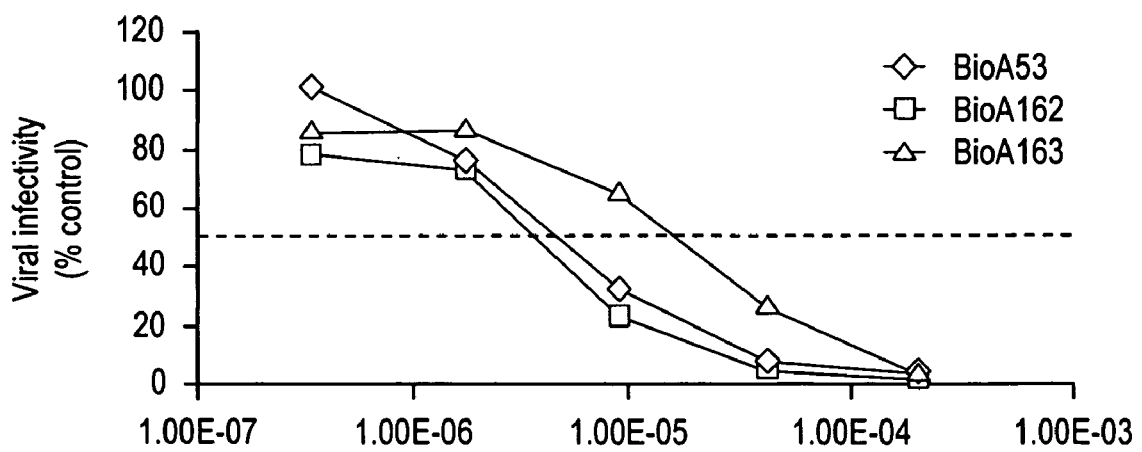
Figure 2A:
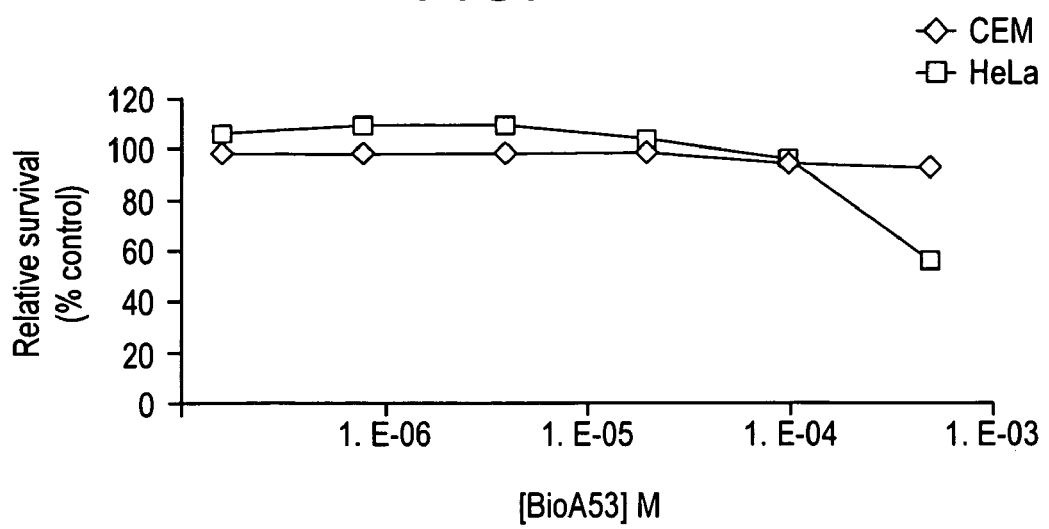
Figure 2B:
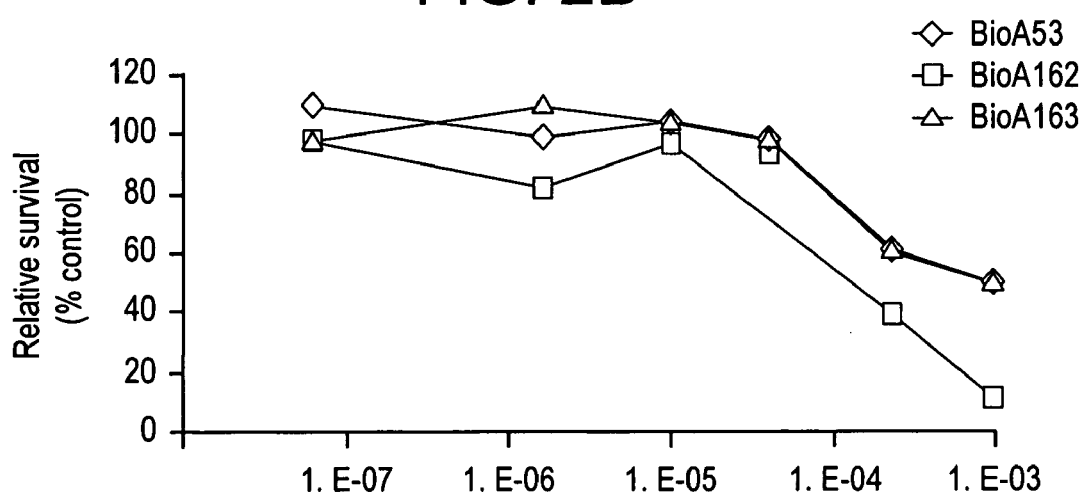
Figure 3:
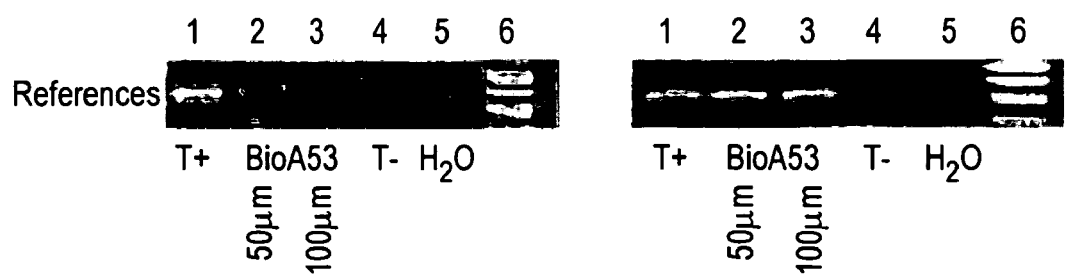

Other characteristics and advantages of the invention are described in the examples which follow, relating to the synthesis of derivatives in accordance with the invention and to the study of their antiviral properties directed against retroviral integrases. In these examples, reference is made to FIGS. 1 to 3, which show, respectively:

FIGS. 1A and 1B, the antiretroviral efficacy of the compounds of the invention,

FIGS. 2A and 2B their lack of toxicity on adherent cells and cells in suspension, and FIGS. 3A and 3B, the inhibition of the entire viral DNA integrated (FIG. 3A) and the detection of the total viral DNA (FIG. 3B).

I) GENERAL SYNTHESIS OF AMIDES 10, HYDRAZIDES 12 AND ALKOXYAMIDES 14

The hydroxy acid 1, previously described in the literature[1], is treated at 100° C. for 72 hours with n-butanol in the presence of polyphosphoric acid[2] so as to give the butyl ester 2. This ester, when treated with pivaloyl chloride in pyridine for 1 hour at 20° C., gives the diester 3. The latter is oxidized by means of selenium dioxide at the reflux temperature of dioxane for 12 hours so as to give the aldehyde 4, which is oxidized to an acid 5 by means of sodium chlorite in a water/tert-butanol mixture for 12 hours, in the presence of sodium dihydrogen phosphate and 2-methyl-2-butene. The succinimidyl quinolinecarboxylate 6 is prepared by fusing the acid 5 with N-hydroxysuccinimide in the presence of dicyclohexylcarbodiimide for 12 hours at 20° C.

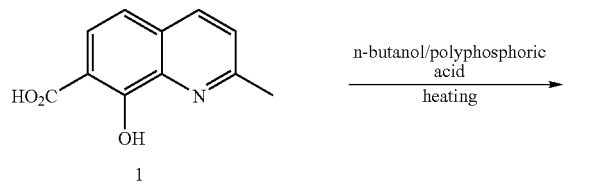

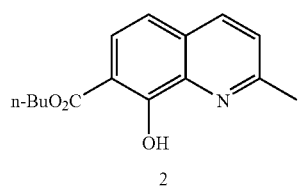

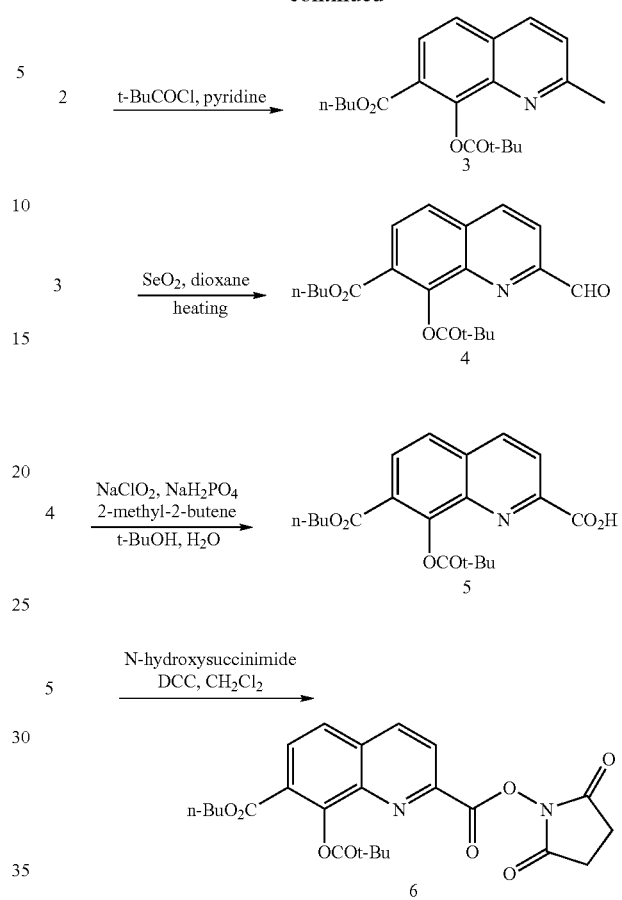

The fusion of succinimidyl quinolinecarboxylate 6 with 3,4-dihydroxybenzylamine p-toluenesulfonate (prepared by catalytic hydrogenation of the corresponding oxime by means of palladium on carbon, in ethanol in the presence of p-toluenesulfonic acid) in pyridine for 12 hours at 20° C., gives the amide 7, which, by saponification with a 3 N sodium hydroxide solution in methanol for 3 hours at 20° C. followed by acidification with dilute sulfuric acid, gives the amide 8.

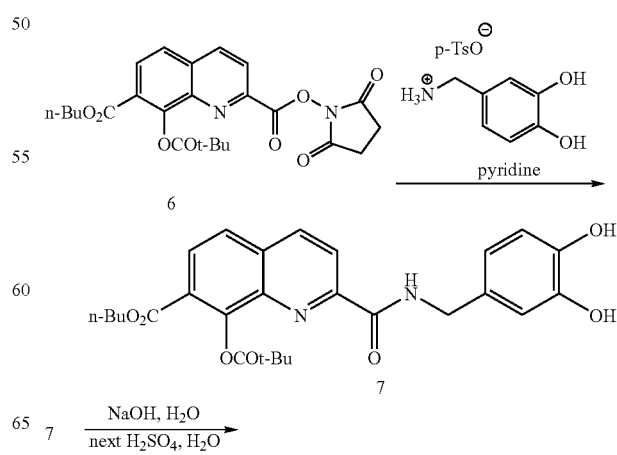

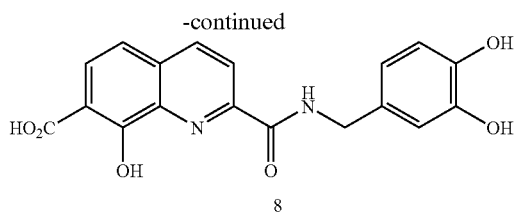

In a similar manner, the fusion of 6 with an amine of general formula 9 gives the amides 10. The fusion of 6 with a hydrazine 11 or a hydroxylamine 13, followed by saponification, gives the hydrazides 12 and the alkoxyamides 14, respectively.

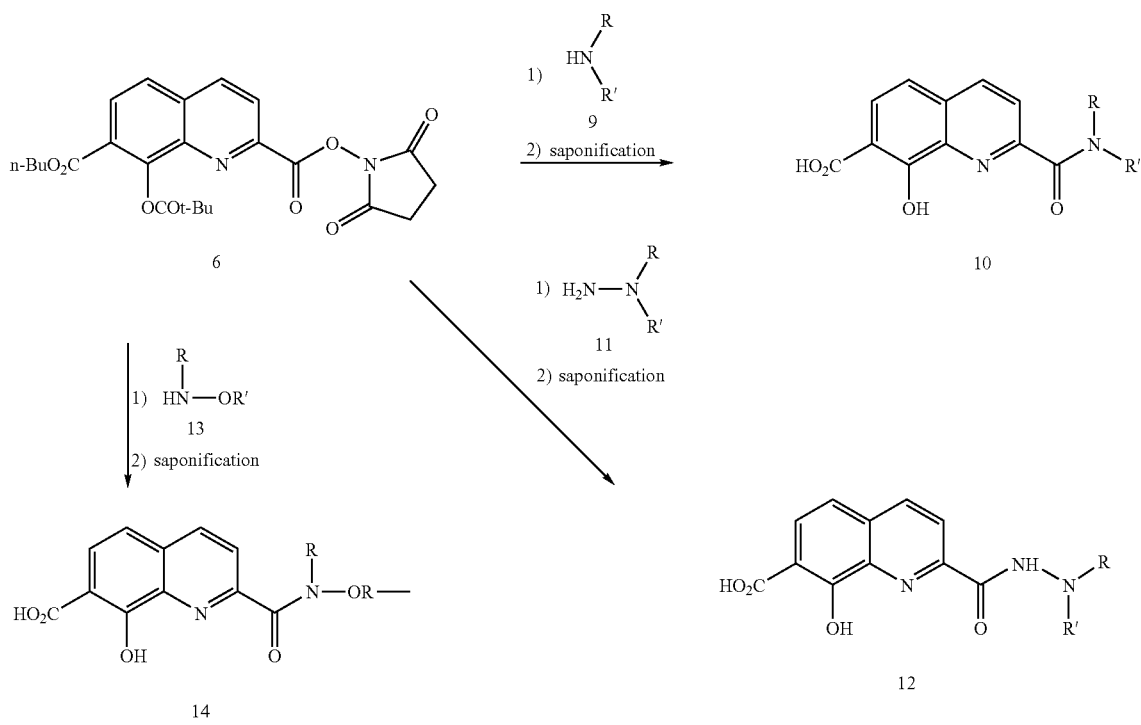

II. DESCRIPTION OF THE PROCEDURES AND PRODUCTS

Synthesis of sodium 2-(3,4-dihydroxybenzylcarbamoyl)-8-hydroxyquinoline-7-carboxylate $1^{st}$ step: preparation of n-butyl 8-hydroxy-2-methylquinoline-7-carboxylate (2)

A mixture of 8-hydroxy-7-quinaldinecarboxylic acid 1 (12 g, 59 mmol) and polyphosphoric acid (30 g) in 60 ml of n-butanol is heated at 100° C. for 72 hours during which additional portions of 30 g of polyphosphoric acid and 30 ml of n-butanol are regularly added every 12 hours. After cooling to 20° C., the reaction mixture is brought to pH 4 with a 6 N potassium hydroxide solution, and then 200 ml of dichloromethane are added. The phases are separated, and the aqueous phase extracted with dichloromethane. The combined organic phases are dried over magnesium sulfate and concentrated under reduced pressure. The residue is chromatographed on a silica column, eluting with a 1/1 cyclohexane/ethyl acetate mixture so as to give 11 g (72%) of n-butyl 8-hydroxy-2-methylquinoline-7-carboxylate in the form of a white solid.

m.p.=50° C.

Rf=0.63 (ethyl acetate)

IR (pure, cm$^{-1}$) v: 1650; 2959

$^1$H NMR (δ in ppm, CDCl$_3$, 200 MHz) 0.90 (t, J=7.4 Hz, 3H); 1.41 (hex, J=7.4 Hz, 2H); 1.70 (quint, J=6.7 Hz, 2H); 2.68 (s, 3H); 4.32 (t, J=6.7 Hz, 2H); 7.09 (d, J=8.7 Hz, 1H); 7.26 (d, J=8.5 Hz, 1H); 7.70 (d, J=8.7 Hz, 1H); 7.86 (d, J=8.5 Hz, 1H)

$^{13}$C NMR (δ in ppm, CDCl$_3$, 50 MHz): 13.6; 19.1; 25.3; 30.5; 65.3; 109.3; 117.3; 124.3; 124.6; 130.3; 135.6; 139.0; 158.4; 159.3; 170.4.

Microanalysis: (C$_{15}$H$_{17}$NO$_3$)

Theory: C 69.48%; H 6.61%; N 5.40%

Exp.: C 69.33%; H 6.77%; N 5.37%

$2^{nd}$ step: preparation of n-butyl 8-(2,2-dimethylpropionyloxy)-2-methylquinoline-7-carboxylate (3)

10.4 ml (84 mmol) of pivaloyl chloride are added, at 0° C., to a solution of the preceding ester 2 (step 1) (11.0 g, 42 mmol) in pyridine (45 ml). After 1 hour at 20° C., the pyridine is distilled under reduced pressure, and then 20 ml of water and 50 ml of dichloromethane are added. The phases are separated and the aqueous phase extracted with dichloromethane. The combined organic phases are dried over magnesium sulfate and concentrated under reduced pressure. The residue is chromatographed on a silica column, eluting with a 2/1 cyclohexane/ethyl acetate mixture so as to give 11.7 g (82%) of n-butyl 8-(2,2-dimethylpropionyloxy)-2-methylquinoline-7-carboxylate 3 in the form of a yellow solid.

m.p.=52° C.

Rf=0.88 (ethyl acetate)

IR (pure, cm$^{-1}$) v: 1725; 1753;

$^1$H NMR (δ in ppm, CDCl$_3$, 200 MHz) 0.86 (t, J=7.5 Hz, 3H); 1.36 (hex, J=7.5 Hz, 2H); 1.46 (s, 9H); 1.65 (quint, J=6.8 Hz, 2H); 2.52 (s, 3H); 4.24 (t, J=6.7 Hz, 2H); 7.17 (d, J=8.4 Hz, 1H); 7.48 (d, J=8.4 Hz, 1H); 7.84 (d, J=8.6 Hz, 2H)

Microanalysis: (C$_{20}$H$_{25}$NO$_4$)
Theory: C 69.95%; H 7.34%; N 4.08%
Exp.: C 70.04%; H 7.40%; N 3.99%

3$^{rd}$ step: preparation of n-butyl 8-(2,2-dimethylpropionyloxy)-2-formylquinoline-7-carboxylate (4)

A mixture of the preceding diester 3 (step 2) (11.5 g, 34 mmol) and selenium dioxide (6.7 g, 60 mmol) in 50 ml of 1,4-dioxane is heated under reflux for 12 hours. After cooling to 20° C., the reaction mixture is filtered on Celite® and concentrated under reduced pressure. The residue is chromatographed on a silica column, eluting a 4/1 cyclohexane/ethyl acetate mixture so as to give 8.6 g (71%) of n-butyl 8-(2,2-dimethylpropionyloxy)-2-formylquinoline-7-carboxylate 4. White solid.

m.p.=108° C.

Rf=0.88 (ethyl acetate)

IR (pure, cm$^{-1}$) v: 1712; 1729; 1752.

$^1$H NMR (δ in ppm, CDCl$_3$, 200 MHz) 0.90 (t, J=7.3 Hz, 3H); 1.41 (hex, J=7.3 Hz, 2H); 1.50 (s, 9H); 1.72 (quint, J=6.7 Hz, 2H); 4.31 (t, J=6.7 Hz, 2H); 7.71 (d, J=8.7 Hz, 1H); 8.00 (d, J=8.4 Hz, 1H); 8.09 (d, J=8.7 Hz, 1H); 8.24 (d, J=8.4 Hz, 1H); 10.05 (s, 1H)

$^{13}$C NMR (δ in ppm, CDCl$_3$, 50 MHz) 13.7; 19.2; 27.5; 30.8; 39.5; 65.5; 119.0; 124.4; 124.8; 129.5; 132.7; 137.2; 141.4; 149.5; 152.8; 164.1; 176.5; 192.7.

Microanalysis: (C$_{20}$H$_{23}$NO$_5$)
Theory: C 67.21%; H 6.49%; N 3.92%
Exp.: C 67.05%; H 6.52%; N 3.90%

4$^{th}$ step: preparation of 8-(2,2-dimethylpropionyloxy)-7-butoxycarbonylquinoline-2-carboxylic acid (5)

A mixture of the preceding aldehyde 4 (step 3) (3.5 g, 10 mmol), sodium dihydrogen phosphate (1.7 g, 12 mmol), 2-methyl-2-butene (6.1 ml, 57 mmol) and sodium chlorite (2.6 g, 29 mmol) is stirred at 20° C. in 160 ml of a 5/1 tert-butanol/water mixture and 30 ml of dichloromethane for 12 hours. The reaction medium is concentrated under reduced pressure. The residue is chromatographed on a silica column, eluting with pure ethyl acetate so as to give 2.4 g (64%) of 8-(2,2-dimethylpropionyloxy)-7-butoxycarbonylquinoline-2-carboxylic acid 5 in the form of white crystals.

m.p.=158° C.

Rf=0.41 (ethyl acetate)

IR (pure, cm$^{-1}$) v: 1693; 1730; 1753.

$^1$H NMR (δ in ppm, CDCl$_3$, 200 MHz) 0.98 (t, J=7.2 Hz, 3H); 1.46 (hex, J=7.2 Hz, 2H); 1.50 (s, 9H); 1.78 (quint, J=6.8 Hz, 2H); 4.35 (t, J=6.8 Hz, 2H); 7.79 (d, J=8.7 Hz, 1H); 8.13 (d, J=8.7 Hz, 1H); 8.29 (d, J=8.5 Hz, 1H); 8.40 (d, J=8.5 Hz, 1H); 9.27 (broad s, 1H)

Microanalysis: (C$_{20}$H$_{23}$NO$_5$)
Theory: C 64.33%; H 6.21%; N 3.75%
Exp.: C 64.33%; H 6.35%; N 3.70%

5$^{th}$ step: preparation of 2,5-dioxopyrrolidin-1-yl 8-(2,2-dimethylpropionyloxy)-7-butoxycarbonylquinolinecarboxylate (6)

A mixture of the preceding acid 5 (step 4) (1.2 g, 3.2 mmol), dicyclohexylcarbodiimide (0.7 g, 3.2 mmol) and N-hydroxysuccinimide (0.4 g, 3.2 mmol) in 12 ml of dichloromethane is stirred at 20° C. for 12 hours. The reaction medium is concentrated under reduced pressure. The residue is chromatographed on a silica column, eluting with a 2/1 cyclohexane/ethyl acetate mixture so as to give 1.2 g (80%) of white crystals of 2,5-dioxopyrrolidin-1-yl 8-(2,2-dimethylpropionyloxy)-7-butoxy-carbonylquinolinecarboxylate 6.

m.p.=143° C.

Rf=0.71 (ethyl acetate)

IR (pure, cm$^{-1}$) v: 1709; 1735; 1736.

$^1$H NMR (δ in ppm, CDCl$_3$, 200 MHz) 0.90 (t, J=7.4 Hz, 3H); 1.42 (hex, J=7.4 Hz, 2H); 1.50 (s, 9H); 1.78 (quint, J=7.0 Hz, 2H); 2.91 (s, 4H); 4.38 (t, J=7.0 Hz, 2H); 7.76 (d, J=8.8 Hz, 1H); 8.17 (d, J=8.8 Hz, 1H); 8.22 (d, J=8.6 Hz, 1H); 8.34 (d, J=8.6 Hz, 1H)

Microanalysis: (C$_{24}$H$_{26}$N$_2$O$_8$)
Theory: C 61.27%; H 5.57%; N 5.95%
Exp.: C 61.39%; H 5.75%; N 6.02%

6$^{th}$ step: preparation of n-butyl 2-(3,4-dihydroxybenzylcarbamoyl)-8-(2,2-dimethylpropionyloxy)quinoline-7-carboxylate (7)

A mixture of the preceding product 6 (step 5) (1.4 g, 2.9 mmol) and 3,4-dihydroxybenzylamine para-toluenesulfonate (0.9 g, 2.9 mmol) in 10 ml of pyridine is stirred at 20° C. for 12 hours. The mixture is concentrated under reduced pressure, and 10 ml of water are added. The mixture is acidified to pH 4 with a 2 N hydrochloric acid solution, and then 20 ml of dichloromethane are added. The phases are separated and the aqueous phase extracted with dichloromethane. The combined organic phases are dried over magnesium sulfate and concentrated under reduced pressure. The residue is chromatographed on a silica column, eluting with a 2/1 cyclohexane/ethyl acetate mixture so as to give 1.1 g (80%) of n-butyl 2-(3,4-dihydroxybenzylcarbamoyl)-8-(2,2-dimethylpropionyloxy)quinoline-7-carboxylate 7. Beige solid.

m.p.=189° C.

Rf=0.73 (ethyl acetate)

IR (pure, cm$^{-1}$) v: 1657; 1719; 1754; 3181; 3369; 3494.

$^1$H NMR (δ in ppm, DMSO-d6, 200 MHz) 0.98 (t, J=7.4 Hz, 3H); 1.41 (s, 9H); 1.45 (hex, J=7.4 Hz, 2H); 1.75 (quint, J=7.0 Hz, 2H); 4.35 (t, J=7.0 Hz, 2H); 4.51 (d, J=5.7 Hz, 2H); 6.07 (t, J=5.7 Hz, 1H, active); 6.63 (dd, J=1.8 Hz, J=8.0 Hz, 1H); 6.77 (d, J=8.0 Hz, 1H); 6.80 (d, J=1.8 Hz, 1H); 7.70 (d, J=8.5 Hz, 1H); 8.05 (d, J=8.5 Hz, 1H); 8.25 (d, J=8.5 Hz, 1H); 8.32 (d, J=8.5 Hz, 1H)

Microanalysis: (C$_{27}$H$_{30}$N$_2$O$_7$)
Theory: C 65.58%; H 6.11%; N 5.66%
Exp.: C 65.57%; H 6.13%; N 5.56%

7$^{th}$ step: preparation of 2-(3,4-dihydroxybenzylcarbamoyl)-8-hydroxyquinoline-7-carboxylic acid (8)

A mixture of the preceding amide 7 (step 6) (0.5 g, 1.0 mmol) and 6.5 ml of a 3 N sodium hydroxide solution in 10 ml of methanol is stirred at 20° C. for 3 hours. The pH is adjusted to 4 with 1 N sulfuric acid solution. The reaction mixture is concentrated under reduced pressure, and then dried under vacuum over phosphoric anhydride. The residue is taken up in 10 ml of anhydrous ethanol in the hot state and the insoluble sodium sulfate is filtered. The filtrate is concentrated under reduced pressure and then taken up in 2 ml of anhydrous ethanol. The medium is cooled: a yellowish solid crystallizes. The latter is washed with dichloromethane, and then dried under vacuum over phosphoric anhydride so as to give 250 mg of acid 8 in the form of a brown solid.

m.p.=232° C. (decomposition)

IR (pure, cm$^{-1}$) v: 1645; 1670; 3249

1H NMR (δ in ppm, DMSO-d6, 200 MHz) 4.40 (d, J=6.2 Hz, 2H); 6.60 (dd, J=1.75 Hz, J=8.04 Hz, 1H); 6.65 (d, J=8.0 Hz, 1H); 6.75 (d, J=1.75 Hz, J=8.04 Hz, 1H); 7.22 (d, J=8.5 Hz, 1H); 7.88 (d, J=8.5 Hz, 1H); 8.15 (d, J=8.5 Hz, 1H); 8.40 (d, J=8.6 Hz, 1H); 8.72 (broad s, 1H); 8.85 (broad s, 1H); 9.27 (t, J=6.2 Hz, 1H)

Microanalysis: ($C_{18}H_{14}N_2O_6$, $1.5H_2O$)
Theory: C 56.69%; H 4.49%; N 7.35%
Exp.: C 57.13%; H 4.17%; N 7.33%

$8^{th}$ step: preparation of sodium 2-(3,4-dihydroxybenzylcarbamoyl)-8-hydroxyquinoline-7-carboxylate A mixture of the preceding amide 8 (step 7) (20 mg, 0.06 mmol) and 0.66 ml of a 0.1 N sodium hydroxide solution are stirred at 20° C. for 10 minutes. The sodium salt obtained is freeze-dried so as to quantitatively give 22 mg of a dark brown solid.

Other Products:

Preparation of 2-(2,4-dihydroxybenzylcarbamoyl)-8-hydroxyquinoline-7-carboxylic acid The same method of preparation as that described for the acid (8) is used.
m.p.=196° C. (decomposition)
IR (pure, cm$^{-1}$) ν: 1624; 1638; 3311.
$^1$H NMR (δ in ppm, DMSO-d6, 200 MHz) 4.45 (d, J=5.8 Hz, 2H); 6.20 (dd, J=2.4 Hz, J=8.2 Hz, 1H); 6.38 (d, J=2.4 Hz, 1H); 7.05 (d, J=8.2 Hz, 1H); 7.34 (d, J=8.7 Hz, 1H); 7.95 (d, J=8.6 Hz, 1H); 8.22 (d, J=8.5 Hz, 1H); 8.50 (d, J=8.6 Hz, 1H); 9.17 (broad s, 1H); 9.28 (t, J=5.8 Hz, 1H); 9.58 (broad s, 1H)

Microanalysis: ($C_{18}H_{14}N_2O_6$, $2H_2O$)
Theory: C 55.39%; H 4.65%; N 7.18%
Exp.: C 55.97%; H 4.57%; N 6.73%

Preparation of 2-(2,3,4-trihydroxybenzylcarbamoyl)-8-hydroxyquinoline-7-carboxylic acid Same method of preparation as for the acid (8).
m.p.=208° C. (decomposition)
IR (pure, cm$^{-1}$) ν: 1625; 1659; 3300.
$^1$H NMR (δ in ppm, DMSO-d6, 200 MHz) 4.45 (d, J=6.0 Hz, 2H); 6.29 (d, J=8.5 Hz, 1H); 6.53 (d, J=8.5 Hz, 1H); 7.40 (d, J=8.8 Hz, 1H); 7.92 (d, J=8.6 Hz, 1H); 8.28 (d, J=8.6 Hz, 1H); 8.52 (d, J=8.5 Hz, 1H); 8.72 (broad s, 1H); 8.89 (broad s, 1H); 9.50 (t, J=6.0 Hz, 1H)

Microanalysis: ($C_{18}H_{14}N_2O_7$, $H_2O$)
Theory: C 55.67%; H 4.15%; N 7.21%
Exp.: C 56.54%; H 4.66%; N 6.31%

III. STUDY OF THE ANTIVIRAL PROPERTIES DIRECTED AGAINST RETROVIRAL INTEGRASES OF THE DERIVATIVES ACCORDING TO THE INVENTION

Presented below, by way of illustration, are the results obtained with sodium 2-(3,4-dihydroxybenzylcarbamoyl)-8-hydroxyquinoline-7-carboxylate, sodium 2-(2,3,4-dihydroxybenzylcarbamoyl)-8-hydroxyquinoline-7-carboxylate and sodium 2-(2,4-dihydroxybenzylcarbamoyl)-8-hydroxyquinoline-7-carboxylate. These compounds will be designated BioA53, BioA162 and BioA163, respectively.

EXAMPLE 1

Inhibition of the Activity in Vitro

The HIV-1 integrase activity is measured by the following tests:

1. The endonucleolytic activity of the recombinant protein is tested on a double-stranded oligonucleotide of 21 base pairs, radiolabeled at the 5' end. The integrase activity results in the removal of the dinucleotide at the 3' end.
2. The test for transfer of strands is carried out with a double-stranded oligonucleotide of 21 base pairs mimicking the end of the viral DNA whose 3' terminal dinucleotide has been removed. The activity of the protein results in the covalent insertion of this oligonucleotide into a homologous oligonucleotide.
3. The disintegration test is carried out with a substrate mimicking the structure of the integrated viral DNA. The quantity of DNA excised by integrase is measured. The latter test measures only the catalytic activity of the protein, excluding its activity for binding to DNA.

The enzymatic activities are tested in the presence of manganese and/or magnesium.

The compounds according to the present invention inhibit the enzymatic activities both in the presence of manganese and magnesium.

EXAMPLE 2

Inhibition of the Replication of the Human Immunodeficiency Virus (HIV-1)

Two tests are used to determine the antiviral efficacy of the compound according to the invention.

The first test consists in bringing cells of an established lymphocytic line, CEM cells, into contact with a supernatant of infected cells containing the infectious virions. The test is carried out in the following manner: the CEM cells, cultured in suspension in RPMI medium supplemented with 10% fetal calf serum, are infected with a viral supernatant with a multiplicity of infection of 0.5. After two hours of infection, the cells are washed twice with RPMI so as to remove the residual viral particles. The cells are then placed again in RPMI medium containing the compound according to the invention. The viral load is evaluated after 72 hours of culture. It is quantified by the following two methods:

1. The quantity of viral protein p24 is determined by an ELISA test.
2. The infectious virus load is estimated by infecting β-gal CD4+ HeLa cells. The efficiency of retroviral integration is estimated by a calorimetric test (CPRG).

The second test consists in bringing β-gal CD4+HeLa cells (human fibroblast cells containing the β-galactosidase gene under the transcriptional control of the Tar viral transactivator and expressing the CD4 membrane receptor) into contact with the supernatant of cells transfected with the plasmid pNL43, containing infectious virions, and the compounds according to the invention. In practice, the β-gal CD4+ HeLa cells are cultured in 96-well plates in DMEM medium supplemented with 10% fetal calf serum, which are brought into contact with 5 ng of p24 (obtained from a transfection of 293T cells with the plasmid pNL43) and dilutions of the compound according to the invention. After 48 hours, the cells are lyzed and β-galactosidase is assayed by CPRG staining.

The results obtained are represented in FIGS. 1A (-♦-BioA53) and 1B (-♦-BioA53; -■-BioA162; -□-BioA163).

In the two tests of activity, the compounds according to the invention show a protective effect against the HIV-1 virus infection. Indeed, this protective effect results in inhibition of the production of viral particles in the first test and an inhibition of CPRG staining in the second test, at micromolar, or even submicromolar, concentrations. As regards the antiretroviral efficiencies, the IC50 values vary from 0.3 µM to 4 µM.

EXAMPLE 3

Cytotoxicity of the Compounds

The toxicity of the compounds is evaluated by a test of biotransformation of MTT to formazan by cellular mitochondrial dehydrogenases.

It is observed that the test compound furthermore lacks cytotoxicity at 500 µM both on adherent cells (HeLa) and cells in suspension (CEM) as illustrated by the results presented in FIGS. 2A (-◆-CEM; -■-HeLa) and 2B (-◆-BioA53; -■-BioA162; -□-BioA163).

EXAMPLE 4

Inhibition of the Integration of Viral DNA into the Host Genome

This test consists in bringing CEM cells into contact with the supernatant of infected cells containing the infectious virions. After 2 hours, the cells are washed and placed again in RPMI medium containing the compound according to the invention for 24 hours (BioA53). The DNA of the cells is then extracted using a genomic DNA preparation kit (QiaBlood, Qiagen™). This DNA is the target for PCR amplifications aimed at evaluating, on the one hand, the quantity of total viral DNA present in the solution, and, on the other hand, the quantity of viral DNA integrated into the cellular genome. The latter amplification takes place in two stages: the first step uses a PCR primer homologous to a sequence of the retroviral DNA; the second primer is homologous to the repetitive genomic Alu sequences. The second stage is a nested PCR which makes it possible to visualize the retroviral DNA.

The quantity of DNA is evaluated by densitometry after separation of the amplification products on agarose gel.

The compound according to the present invention shows a decrease of at least 80% in the quantity of DNA integrated for a concentration of 50 µM and an inhibition of the entire DNA integrated at 100 µM (FIG. 3A) whereas the quantity of total viral DNA is not affected by the treatment of cells with the compound (FIG. 3B).

EXAMPLE 5

Preparation of Tablets

Tablets containing BioA53 are prepared by carrying out the procedure as follows:

A therapeutically active quantity of the compound BioA53, corn starch and microcrystalline cellulose are added to an aqueous solution of hydroxypropylcellulose. The mixture is passed through a sieve so as to produce granules. After drying, they are mixed with magnesium stearate and formulated into 250 mg tablets according to the usual techniques.

BIBLIOGRAPHIC REFERENCES

1—Meek, W. H.; Fuschman, C. H. J.; *J. Chem. Eng. Data* 1969, 14, 388–391.
2—Bader, A. R.; Kontowicz, A. D. *J. Am. Chem. Soc.* 1953, 75, 5416–5417.
3—Epstein, J., Michel, H. O., Rosenblatt, D. H., Plapinger, R. E., Stephani, R. A., Cook, E., *J. Am. Chem. Soc.* 1964, 86, 4959–4963.

What is claimed is:

1. A 2-carbamoyl-8-hydroxyquinoline-7-carboxylic acid compound or its pharmaceutically acceptable salt, wherein said compound corresponds to formula I:

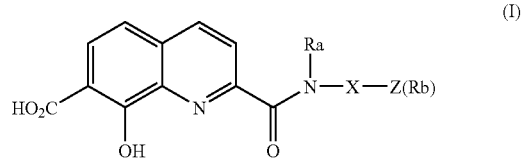

(I)

in which
X represents an alkyl-$(CH_2)_n$— chain in which n is equal to 0, 1 or 2, O, or N,
Z represents an aromatic ring which may contain heteroatoms chosen from O, N or S, as substitutions for the carbon atoms constituting said aromatic ring, it being possible or otherwise for this ring to be substituted with Rb,
Rb represents 1 to 3 identical or different substituents chosen from the group —OH, —OR, —COOH, —COOR, —COH, —COR, —NH₂, —NH(R), —NH (R, R'), —SH, —SR and CN,
Ra represents a hydrogen atom or a group —$(CH_2)_{n'}$—Y, for which n' is equal to 0, 1, 2 or 3 and Y represents CR₃, —COOR, —COOR, —CN, —OH, —OR, SR, or an aryl group optionally substituted with Rb,
R and R', which are identical or different, represent a linear or branched alkyl chain of 1 to 4 carbon atoms.

2. A 2-carbamoyl-8-hydroxyquinoline-7-carboxylic acid compound, chosen from 2-(3,4-dihydroxybenzylcarbamoyl)-8-hydroxyquinoline-7-carboxylic acid and 2-(2,4-dihydroxybenzylcarbamoyl)-8-hydroxyquinoline-7-carboxylic acid and a sodium salt of said compound.

3. A compound according to claim 1, wherein:
X represents a —$(CH_2)_n$— chain in which n is 0 or 1;
Z represents a phenyl group;
Rb represents 1 to 3 OH group;
Ra represents a hydrogen atom.

4. A method for synthesizing the compound as claimed in claim 1, comprising the reaction of the succinimidyl quinolinecarboxylate of formula II

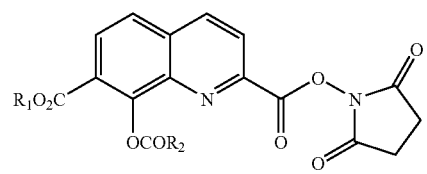

II in which R₁ and R₂, which are identical or different, represent alkyl radicals of 1 to 4C, with an amine of formula III

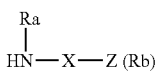

(III)

where appropriate in the form of a salt, followed by saponification and, where appropriates, acidification.

5. The method as claimed in claim 4, comprising preparing a compound of formula IA with an amide spacer arm,

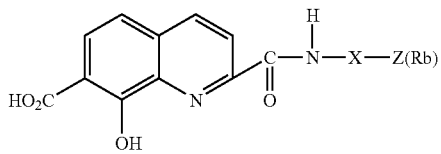

(IA)

in which Rb and Z are as defined above, and X represents a group —$(CH_2)_n$— as defined above, a succinimidyl quinolinecarboxylate of formula II is reacted with an amine salt of the following formula IV:

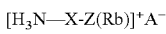

(IV)

in which Z and Rb are as defined above, X=$(CH_2)_n$ as defined above, and $A^-$ is an anion of an organic salt or a halide, the amide compound being recovered by saponification, followed by acidification.

6. The method as claimed in claim 4, comprising preparing a compound of formula IB with a substituted amide spacer arm,

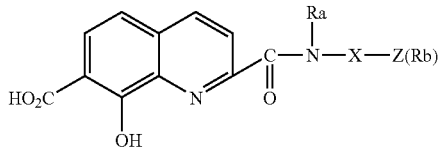

(IB)

in which Rb and Z are as defined above, and X represents a known group —$(CH_2)_n$— defined above, the compound of formula II is reacted with an amine of the following formula V:

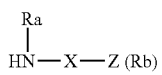

(V)

in which the substituents are as defined above, this reaction being followed by saponification.

7. The method as claimed in claim 4, comprising preparing a compound of formula IC with a hydrazide spacer arm,

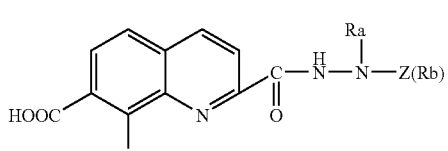

(IC)

in which the different substituents are as defined above, the compound of formula II is reacted with the hydrazine of the following formula VI:

(VI)

8. The method as claimed in claim 4, comprising preparing a compound of formula ID with an alkoxyamide spacer arm,

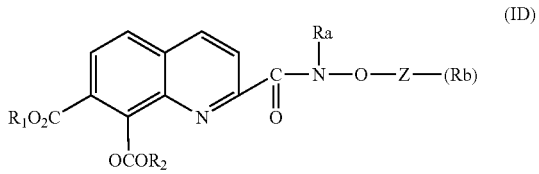

(ID)

in which the different substituents are as defined above, the compound of formula II is reacted with the hydroxylamine of the following formula VII:

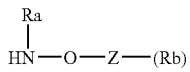

(VII)

in which Ra, Rb and Z are as defined above.

9. The method as claimed in claim 4, wherein the protected quinoline compound of formula II is obtained from a quinoline hydroxy acid of formula VIII:

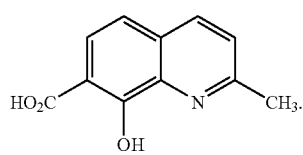

(VIII)

10. The method as claimed in claim 9, wherein said method comprises the protection of the —COOH and —OH groups with the aid of a compound capable of generating protective groups that are specific in relation to the relevant functional groups and that can be selectively cleaved without adversely affecting the remainder of the molecule.

11. The method according to claim 5, wherein said amine salt is a paratoluenesulfonate.

12. A pharmaceutical composition, comprising an effective quantity of at least one compound as defined in either of claims 1 and 2 in combination with pharmaceutically acceptable vehicles.

* * * * *